（12) United States Patent
Kesten et al.

(10) Patent No.: US 9,333,070 B2
(45) Date of Patent: May 10, 2016

(54) BREAST IMPLANT WITH INTERNAL FLOW DAMPENING

(71) Applicant: Evera Medical, Inc., Portola Valley, CA (US)

(72) Inventors: Randy J. Kesten, Los Altos, CA (US); Michael D. Lesh, Mill Valley, CA (US)

(73) Assignee: Evera Medical, Inc., Portola Valley, CA (US)

( * ) Notice: Subject to any disclaimer, the term of this patent is extended or adjusted under 35 U.S.C. 154(b) by 147 days.

(21) Appl. No.: 14/042,457

(22) Filed: Sep. 30, 2013

(65) Prior Publication Data

US 2014/0135923 A1 May 15, 2014

Related U.S. Application Data

(63) Continuation of application No. 12/024,835, filed on Feb. 1, 2008, now abandoned.

(51) Int. Cl.
*A61F 2/12* (2006.01)
*A61F 2/00* (2006.01)
*A61F 2/52* (2006.01)

(52) U.S. Cl.
CPC .............. *A61F 2/12* (2013.01); *A61F 2/0059* (2013.01); *A61F 2/0077* (2013.01); *A61F 2/52* (2013.01); *A61F 2230/0034* (2013.01); *A61F 2230/0093* (2013.01); *A61F 2250/001* (2013.01); *A61F 2250/0003* (2013.01); *A61F 2250/0009* (2013.01); *A61F 2250/0012* (2013.01); *A61F 2250/0013* (2013.01); *A61F 2250/0015* (2013.01); *A61F 2250/0024* (2013.01); *A61F 2250/0025* (2013.01); *A61F 2250/0028* (2013.01); *A61F 2250/0051* (2013.01)

(58) Field of Classification Search
CPC ............ A61F 2/12; A61F 2/52; A61F 2/0059
See application file for complete search history.

(56) References Cited

U.S. PATENT DOCUMENTS

| | | |
|---|---|---|
| 2,512,568 A | 6/1950 | Saffir |
| 3,293,663 A | 12/1966 | Cronin |
| 3,366,975 A | 2/1968 | Pangman |
| 3,919,724 A | 11/1975 | Sanders et al. |
| 3,934,274 A | 1/1976 | Hartley, Jr. et al. |

(Continued)

FOREIGN PATENT DOCUMENTS

| | | |
|---|---|---|
| EP | 0322194 | 6/1989 |
| EP | 0357927 | 3/1990 |

(Continued)

OTHER PUBLICATIONS

International Search Report and Written Opinion of the International Searching Authority for International Application No. PCT/US2009/032259, mailed on Mar. 16, 2009, in 14 pages.

(Continued)

*Primary Examiner* — Andrew Iwamaye
(74) *Attorney, Agent, or Firm* — Knobbe, Martens, Olson & Bear LLP

(57) ABSTRACT

An implantable prosthesis is provided having a membrane which holds a flowable substance. The membrane is separated into a first chamber and a second chamber with the first and second chambers being fluidly coupled via an orifice. The orifice has a size which may be adjusted by the user after implanting the prosthesis into the patient.

15 Claims, 16 Drawing Sheets

(56) References Cited

U.S. PATENT DOCUMENTS

| | | |
|---|---|---|
| 3,949,073 A | 4/1976 | Daniels et al. |
| 3,953,566 A | 4/1976 | Gore |
| 4,051,840 A | 10/1977 | Kantrowitz et al. |
| 4,187,390 A | 2/1980 | Gore |
| 4,327,734 A | 5/1982 | White, Jr. |
| 4,383,929 A | 5/1983 | Bertocchio |
| 4,395,806 A | 8/1983 | Wonder et al. |
| 4,433,440 A | 2/1984 | Cohen |
| 4,517,979 A | 5/1985 | Pecenka |
| 4,531,244 A | 7/1985 | Hamas |
| 4,543,088 A | 9/1985 | Bootman |
| 4,545,367 A | 10/1985 | Tucci |
| 4,592,755 A | 6/1986 | Penton et al. |
| 4,631,188 A | 12/1986 | Stoy et al. |
| 4,643,733 A | 2/1987 | Becker |
| 4,648,880 A | 3/1987 | Brauman |
| 4,664,655 A | 5/1987 | Orentreich et al. |
| 4,738,657 A | 4/1988 | Hancock |
| 4,820,303 A | 4/1989 | Brauman |
| 4,828,561 A | 5/1989 | Woodroof |
| 4,828,827 A | 5/1989 | Henderson et al. |
| 4,840,615 A | 6/1989 | Hancock |
| 4,863,470 A | 9/1989 | Carter |
| 4,904,260 A | 2/1990 | Ray et al. |
| 4,908,029 A | 3/1990 | Bark |
| 4,917,646 A | 4/1990 | Kieves |
| 4,944,749 A | 7/1990 | Becker |
| 4,955,907 A | 9/1990 | Ledergerber |
| 4,963,150 A | 10/1990 | Brauman |
| 4,966,478 A | 10/1990 | Kuo |
| 4,969,901 A | 11/1990 | Binder |
| 4,994,028 A | 2/1991 | Leonard et al. |
| 5,007,929 A | 4/1991 | Quaid |
| 5,019,101 A | 5/1991 | Purkait et al. |
| 5,074,878 A | 12/1991 | Bark et al. |
| 5,098,779 A | 3/1992 | Kranzler et al. |
| 5,102,389 A | 4/1992 | Hauser |
| 5,116,387 A | 5/1992 | Berg |
| 5,123,905 A | 6/1992 | Kelman |
| 5,141,508 A | 8/1992 | Bark et al. |
| 5,181,921 A | 1/1993 | Makita et al. |
| 5,188,558 A | 2/1993 | Barton et al. |
| 5,213,574 A | 5/1993 | Tucker |
| 5,273,532 A | 12/1993 | Niezink et al. |
| 5,282,856 A | 2/1994 | Ledergerber |
| 5,324,259 A | 6/1994 | Taylor et al. |
| 5,356,429 A | 10/1994 | Seare |
| 5,376,117 A | 12/1994 | Pinchuk et al. |
| 5,387,192 A | 2/1995 | Glantz |
| 5,425,747 A | 6/1995 | Brotz |
| 5,425,760 A | 6/1995 | Rosenberg |
| 5,437,900 A | 8/1995 | Kuzowski |
| 5,454,788 A | 10/1995 | Walker et al. |
| 5,456,716 A | 10/1995 | Iverson et al. |
| 5,461,781 A | 10/1995 | Zukoski |
| 5,480,430 A | 1/1996 | Carlisle |
| 5,496,345 A | 3/1996 | Kieturakis et al. |
| 5,496,367 A | 3/1996 | Fisher |
| 5,496,370 A | 3/1996 | Hamas |
| 5,514,153 A | 5/1996 | Bonutti |
| 5,545,217 A | 8/1996 | Offray et al. |
| 5,545,220 A | 8/1996 | Andrews et al. |
| 5,549,672 A | 8/1996 | Maddock et al. |
| 5,558,641 A | 9/1996 | Glantz |
| 5,558,829 A | 9/1996 | Petrick |
| 5,571,189 A | 11/1996 | Kuslich |
| RE35,391 E | 12/1996 | Brauman |
| 5,582,585 A | 12/1996 | Nash-Morgan |
| 5,584,859 A | 12/1996 | Brotz |
| 5,599,852 A | 2/1997 | Scopelianos et al. |
| 5,607,477 A | 3/1997 | Schindler et al. |
| 5,630,843 A | 5/1997 | Rosenberg |
| 5,630,844 A | 5/1997 | Dogan et al. |
| 5,632,777 A | 5/1997 | Petrick |
| 5,633,001 A | 5/1997 | Agerup |
| 5,643,783 A | 7/1997 | Olsen et al. |
| 5,645,081 A | 7/1997 | Årgenta et al. |
| 5,645,558 A | 7/1997 | Horton |
| 5,645,597 A | 7/1997 | Krapiva |
| 5,653,755 A | 8/1997 | Ledergerber |
| 5,653,757 A | 8/1997 | Petrick |
| 5,658,330 A | 8/1997 | Carlisle et al. |
| 5,660,849 A | 8/1997 | Polson et al. |
| 5,674,285 A | 10/1997 | Quaid |
| 5,702,677 A | 12/1997 | Shimp et al. |
| 5,725,507 A | 3/1998 | Petrick |
| 5,728,752 A | 3/1998 | Scopelianos et al. |
| 5,779,672 A | 7/1998 | Dormandy, Jr. |
| 5,779,734 A | 7/1998 | Ledergerber |
| 5,782,913 A | 7/1998 | Schindler et al. |
| 5,795,325 A | 8/1998 | Valley et al. |
| 5,798,096 A | 8/1998 | Pavlyk |
| 5,824,081 A | 10/1998 | Knapp et al. |
| 5,861,032 A | 1/1999 | Subramaniam |
| 5,863,297 A | 1/1999 | Walter et al. |
| 5,871,537 A | 2/1999 | Holman et al. |
| 5,922,025 A | 7/1999 | Hubbard |
| 5,931,855 A | 8/1999 | Buncke |
| 5,935,164 A | 8/1999 | Iversen |
| 5,935,362 A | 8/1999 | Petrick |
| 5,941,910 A | 8/1999 | Schindler et al. |
| 5,944,738 A | 8/1999 | Amplatz et al. |
| D413,672 S | 9/1999 | Fogarty |
| 5,957,939 A | 9/1999 | Heaven et al. |
| 5,961,552 A | 10/1999 | Iversen et al. |
| 5,964,261 A | 10/1999 | Neuenfeldt et al. |
| 5,964,803 A | 10/1999 | Iversen |
| 5,984,943 A | 11/1999 | Young |
| 5,989,214 A | 11/1999 | van de Wijdeven |
| 5,989,216 A | 11/1999 | Johnson |
| 5,997,574 A | 12/1999 | Hayes et al. |
| 6,039,712 A | 3/2000 | Fogarty |
| 6,053,899 A | 4/2000 | Slanda et al. |
| 6,060,639 A | 5/2000 | Petrick |
| 6,090,063 A | 7/2000 | Makower et al. |
| 6,098,629 A | 8/2000 | Johnson et al. |
| 6,146,418 A | 11/2000 | Berman |
| 6,162,251 A | 12/2000 | Kredovski |
| 6,171,298 B1 | 1/2001 | Matsuura et al. |
| 6,187,043 B1 | 2/2001 | Ledergerber |
| 6,214,045 B1 | 4/2001 | Corbitt, Jr. et al. |
| 6,228,116 B1 | 5/2001 | Ledergerber |
| 6,231,586 B1 | 5/2001 | Mariant |
| 6,231,613 B1 | 5/2001 | Greff et al. |
| 6,241,747 B1 | 6/2001 | Ruff |
| 6,251,137 B1 | 6/2001 | Andrews et al. |
| 6,258,055 B1 | 7/2001 | McCrory et al. |
| 6,261,316 B1 | 7/2001 | Shaolian et al. |
| 6,261,323 B1 | 7/2001 | Neto |
| 6,264,700 B1 | 7/2001 | Kilcoyne et al. |
| 6,267,772 B1 | 7/2001 | Mulhauser et al. |
| 6,270,517 B1 | 8/2001 | Brotz |
| 6,277,150 B1 | 8/2001 | Crawley et al. |
| 6,296,624 B1 | 10/2001 | Gerber et al. |
| 6,299,590 B1 | 10/2001 | Luscher et al. |
| 6,312,405 B1 | 11/2001 | Meyer et al. |
| 6,315,796 B1 | 11/2001 | Eaton |
| 6,322,576 B1 | 11/2001 | Wallace et al. |
| 6,379,329 B1 | 4/2002 | Naglreiter et al. |
| 6,402,784 B1 | 6/2002 | Wardlaw |
| 6,440,098 B1 | 8/2002 | Luscher |
| 6,451,052 B1 | 9/2002 | Burmeister et al. |
| 6,458,119 B1 | 10/2002 | Berenstein et al. |
| 6,470,216 B1 | 10/2002 | Knowlton |
| 6,471,689 B1 | 10/2002 | Joseph et al. |
| 6,478,656 B1 | 11/2002 | Khouri |
| 6,478,809 B1 | 11/2002 | Brotz |
| RE37,950 E | 12/2002 | Dunn et al. |
| 6,520,989 B1 * | 2/2003 | Eaton ................. 623/7 |
| 6,530,896 B1 | 3/2003 | Elliott |
| 6,537,242 B1 | 3/2003 | Palmer |
| 6,544,287 B1 | 4/2003 | Johnson et al. |
| 6,551,342 B1 | 4/2003 | Shen et al. |
| 6,578,580 B2 | 6/2003 | Conrad et al. |

(56) References Cited

U.S. PATENT DOCUMENTS

| | | |
|---|---|---|
| 6,585,748 B1 | 7/2003 | Jeffree |
| 6,599,310 B2 | 7/2003 | Leung et al. |
| 6,629,947 B1 | 10/2003 | Sahatjian et al. |
| 6,648,853 B1 | 11/2003 | McEntee |
| 6,652,544 B2 | 11/2003 | Houser et al. |
| 6,660,301 B1 | 12/2003 | Vogel et al. |
| 6,663,596 B2 | 12/2003 | Griego et al. |
| 6,673,105 B1 | 1/2004 | Chen |
| 6,684,107 B1 | 1/2004 | Binder |
| 6,699,176 B1 | 3/2004 | Khouri |
| 6,702,731 B2 | 3/2004 | Milbocker |
| 6,716,251 B1 | 4/2004 | Asius et al. |
| 6,725,866 B2 | 4/2004 | Johnson et al. |
| 6,740,082 B2 | 5/2004 | Shadduck |
| 6,743,208 B1 | 6/2004 | Coyle |
| 6,755,861 B2 | 6/2004 | Nakao |
| 6,802,861 B1 | 10/2004 | Hamas |
| 6,878,137 B2 | 4/2005 | Benchetrit |
| 6,899,713 B2 | 5/2005 | Shaolian et al. |
| 6,921,418 B2 | 7/2005 | Ledergerber |
| 7,077,865 B2 | 7/2006 | Bao et al. |
| 7,094,230 B2 | 8/2006 | Flaherty et al. |
| 7,244,270 B2 | 7/2007 | Lesh |
| 7,641,688 B2 | 1/2010 | Lesh |
| 7,758,649 B2 * | 7/2010 | Walsh et al. ............... 623/17.16 |
| 7,998,201 B2 | 8/2011 | Lesh |
| 7,998,202 B2 | 8/2011 | Lesh |
| 8,556,968 B2 | 10/2013 | Hamas et al. |
| 2002/0019670 A1 | 2/2002 | Crawley et al. |
| 2002/0022861 A1 | 2/2002 | Jacobs et al. |
| 2002/0025340 A1 | 2/2002 | Dyer |
| 2003/0028147 A1 | 2/2003 | Aves et al. |
| 2003/0074021 A1 | 4/2003 | Morriss et al. |
| 2003/0074084 A1 | 4/2003 | Nakao |
| 2003/0225453 A1 | 12/2003 | Murch |
| 2004/0037887 A1 | 2/2004 | Bourne et al. |
| 2004/0176841 A1 | 9/2004 | Ferguson |
| 2004/0243157 A1 | 12/2004 | Connor et al. |
| 2004/0249457 A1 | 12/2004 | Smith et al. |
| 2005/0131325 A1 | 6/2005 | Chen et al. |
| 2005/0177234 A1 | 8/2005 | Raphael |
| 2005/0187624 A1 | 8/2005 | Corbitt, Jr. |
| 2006/0058735 A1 | 3/2006 | Lesh |
| 2006/0058890 A1 | 3/2006 | Lesh |
| 2006/0058891 A1 | 3/2006 | Lesh |
| 2006/0058892 A1 | 3/2006 | Lesh |
| 2006/0136070 A1 | 6/2006 | Pinchuk |
| 2006/0161253 A1 | 7/2006 | Lesh |
| 2006/0282164 A1 | 12/2006 | Seastrom |
| 2008/0015498 A1 | 1/2008 | Lesh |
| 2008/0221678 A1 | 9/2008 | Hamas |
| 2008/0221679 A1 | 9/2008 | Hamas |
| 2008/0275569 A1 | 11/2008 | Lesh |
| 2009/0024215 A1 | 1/2009 | Lesh |
| 2009/0024227 A1 | 1/2009 | Lesh |
| 2009/0024228 A1 | 1/2009 | Lesh |
| 2009/0048684 A1 | 2/2009 | Lesh |
| 2009/0125107 A1 | 5/2009 | Maxwell |
| 2009/0149953 A1 | 6/2009 | Schuessler et al. |
| 2009/0198328 A1 | 8/2009 | Kesten et al. |
| 2009/0198330 A1 | 8/2009 | Kesten et al. |
| 2009/0198331 A1 | 8/2009 | Kesten et al. |
| 2010/0087922 A1 | 4/2010 | Hamas |
| 2010/0133133 A1 | 6/2010 | Hamas |
| 2010/0249946 A1 | 9/2010 | Lesh et al. |
| 2010/0249947 A1 | 9/2010 | Lesh et al. |
| 2014/0163696 A1 | 6/2014 | Lesh et al. |

FOREIGN PATENT DOCUMENTS

| | | |
|---|---|---|
| EP | 0411767 | 3/1991 |
| RU | 2 158 552 C2 | 11/2000 |
| WO | WO 95/22359 | 8/1995 |
| WO | WO 96/11647 | 4/1996 |
| WO | WO 98/37836 | 9/1998 |
| WO | WO 99/17816 | 4/1999 |

OTHER PUBLICATIONS

Homicz, Mark R., M.D. et al., Review of Injectable Materials for Soft Tissue Augmentation, *Facial Plastic Surgery*, vol. 20, No. 1, 2004.

Sciafani, Anthony P. et al., Collagen, Human Collagen, and Fat: The Search for a Three-Dimensional Soft Tissue Filler, *Facial Plastic Surgery*, vol. 17, No. 1, 2001.

Wall, Stephen J., M.D., Ph.D. et al., Patient Satisfaction with Expanded Polytetrafluoroethylene (Softform) Implants to the Perioral Region, *Arch Facial Plast Surg*. vol. 5, Jul./Aug. 2003.

* cited by examiner

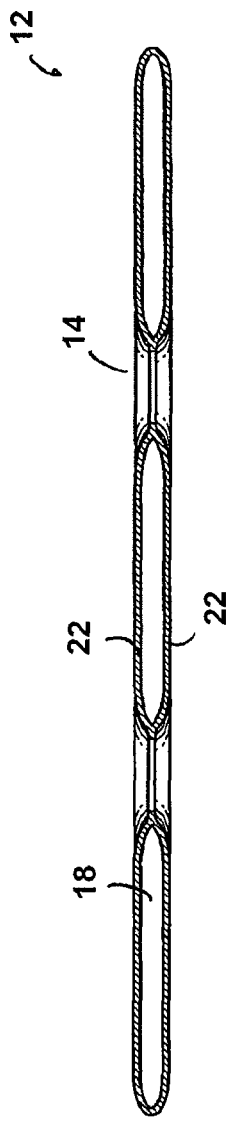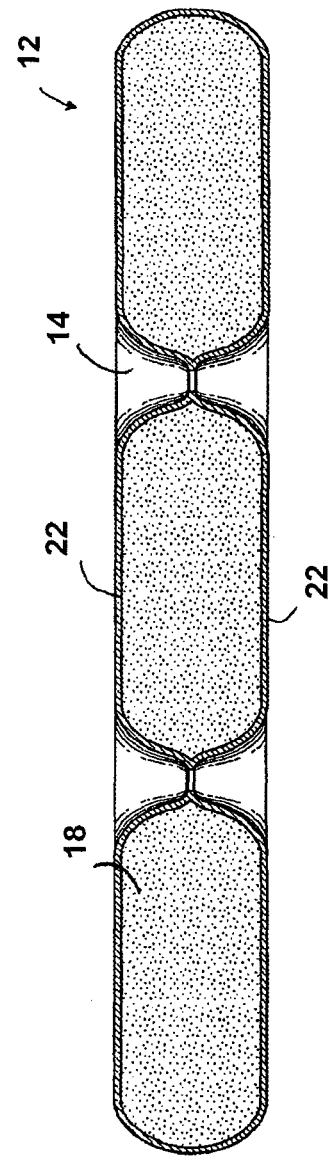
FIG 3
FIG 4

BREAST IMPLANT WITH INTERNAL FLOW DAMPENING

CROSS-REFERENCE TO RELATED APPLICATIONS

The present application is a continuation application of U.S. patent application Ser. No. 12/024,835 filed Feb. 1, 2008, which is hereby incorporated by reference herein in its entirety.

BACKGROUND OF THE INVENTION

The present invention is directed to an implantable prosthesis which may be used anywhere in the body such as the breast.

An implant provides support for the surrounding body tissue and occupies voids created by the removal of tissue to preserve the normal outward appearance and feel of the body. Prosthetic devices have also been used to enhance or augment the appearance of body parts.

Breast prostheses have long been used for breast augmentation and for reconstruction such as following a mastectomy. The prostheses are available in numerous sizes and shapes including teardrop, round and low profile. Usually, breast prostheses are implanted via a small inframammary or pariaerolar incision into a pocket dissected deep into the patient's own breast tissue in front of the pectoral muscle. In certain situations, the prosthesis may be placed behind the various chest muscles.

Some prosthetic devices have utilized an outer shell or envelope which is filled with a flowable substance such as silicone gel or saline. These prior art devices have tactile properties similar to normal tissue but suffer from certain disadvantages. Saline filled prosthetic devices can lack the proper appearance and tactile properties of normal tissue. Saline displaces relatively quickly and can create a fluid wave in the implant which presents an unnatural look and an audible sound. Saline filled implants also lack form stability which may result in the implant folding over itself or visible wrinkling.

The object of the present invention is to overcome some of the drawbacks of the prior art implants. The object of the present invention is to construct a surgically implantable prosthetic device which may be filled with saline and/or other fluids and which has desirable tactile appearance and other characteristics.

SUMMARY OF THE INVENTION

The implantable prosthesis of the present invention includes a membrane and an open cell structure contained within the membrane. The open cell structure dampens fluid motion within the membrane to reduce some of the problems with prior art devices as described above.

In one aspect of the invention, the implantable prosthesis has an orifice of adjustable size. The orifice provides fluid communication between a first chamber and a second chamber in the membrane. The size of the orifice may be adjusted after implantation of the prosthesis using a control element.

In another aspect of the present invention, an implantable prosthesis is provided which has a tension element extending between two locations on the membrane. The tension on the tension element may be altered before or after introduction of the prosthesis into the patient. The tension element may extend through a seal which permits tensioning of the tension element while preventing the flowable substance from leaking out of the membrane.

In a further aspect of the present invention, the open-cell structure may have a plurality of voids which are substantially larger than the cells of the open-cell structure. The voids may be symmetrically positioned relative to an axis of symmetry in the membrane.

In still another aspect of the present invention, the open cell structure may have a natural, unbiased shape which is larger than the membrane. The open cell structure is compressed and positioned within the membrane so that the membrane holds the open cell structure in a collapsed shape.

The open cell structure may also include a channel extending along an outer surface of the open cell structure and adjacent to the inner surface of the membrane. The channel enhances fluid flow in this region and, in particular, in the area between the membrane and the open cell structure. The channels may be oriented radially with respect to an apex of the membrane, circumferentially or in any other suitable manner.

A plurality of spacers may also be used between the open cell structure and the membrane. The spacers provide an area between the membrane and the open cell structure which enhances fluid flow in the area between the membrane and open cell structure. The spacers may be attached to the external surface of the open cell structure or to the inner surface of the membrane.

The open cell structure may be selectively attached to the membrane at discrete locations which are separated by areas where the open cell structure is free to slide against the inner surface of the membrane. The attachments may be along the anterior wall and/or posterior wall so that portions of the anterior and/or posterior wall are free of attachments to the open cell structure. The attachments may be along a continuous strip of the membrane which, for example, forms a loops that encircles the apex of the membrane.

These and other features of the present invention will become apparent from the following description of the preferred embodiments.

BRIEF DESCRIPTION OF THE DRAWINGS

FIG. 3 shows an internal wall having an orifice.
FIG. 4 shows the internal wall in an expanded shape which reduces the size of the orifice.
FIG. 16 shows an open cell structure.

DETAILED DESCRIPTION OF THE PREFERRED EMBODIMENT

Figure 1:
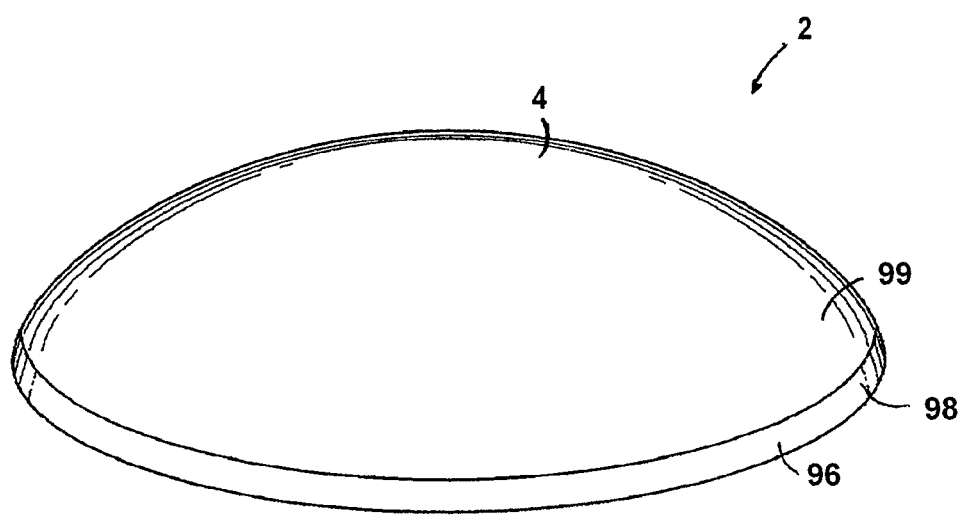
FIG. 1 shows an implantable prosthesis.
Figure 2:
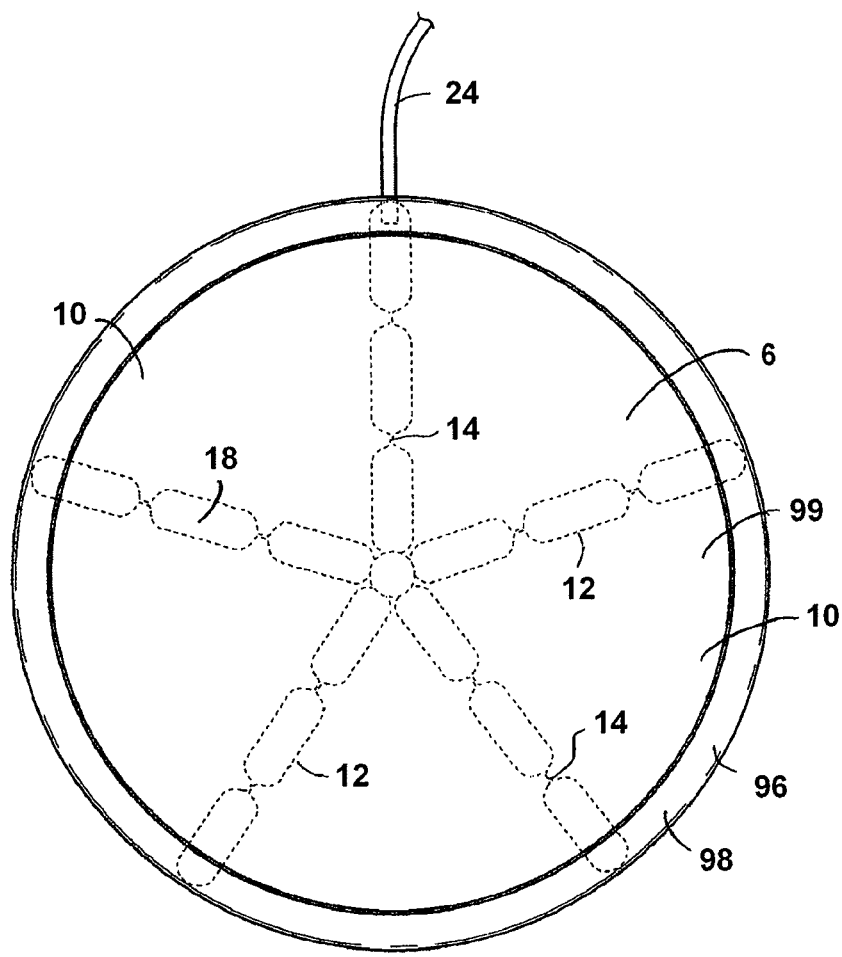
FIG. 2 is a top view of the implantable prosthesis of FIG. 1.
Figure 5:
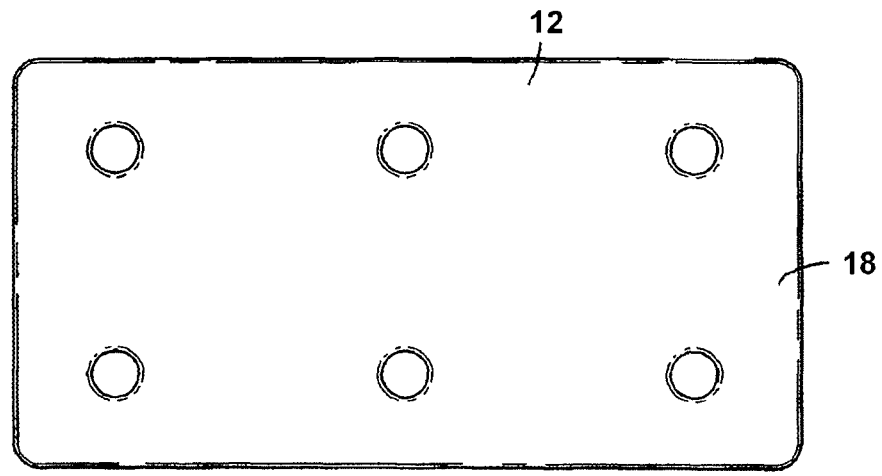
FIG. 5 shows the internal wall separated from the rest of the prosthesis.
Figure 6:
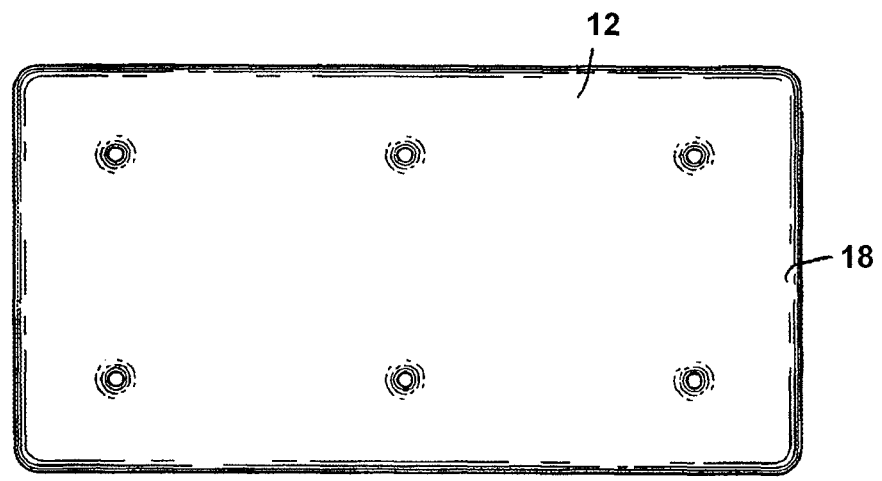
FIG. 6 shows the internal wall expanded to collapse the orifice.

Referring to FIGS. 1-6, an implantable prosthesis 2 is shown. The prosthesis 2 includes a membrane 4 which may be made formed in any suitable manner. The membrane 4 contains a flowable substance 6 such as silicone gel, saline or any other suitable substance. The flowable substance 6 may also include elements (not shown), such as beads or spheres, which are suspended in the flowable substance 6 without departing from the scope of the invention. Any of the embodiments disclosed herein may incorporate features, structures and materials disclosed in U.S. patent application Ser. No. 11/316,215 to Michael Lesh, entitled Tissue Augmentation Device filed Dec. 22, 2005, the disclosure of which is incorporated in its entirety herein by reference.

The membrane 4 is divided into a number of chambers 10 separated by walls 12. The walls 12 each have one or more orifices 14 which have a size which may be adjusted. Changing the size of the orifices 14 in the walls 12 alters the flow characteristics of the prosthesis 2 in that a smaller orifice 14 will provide a slower flow rate of the flowable substance 6 between the chambers 10. The chambers 10 may also be filled with a substance which further reduces the flow rate of fluid such as an open-cell structure which may be a matrix of material, a sponge, a foam or any other suitable open-cell structure which reduces the flow rate of fluid within the membrane 4 as described below in connection with other preferred embodiments.

The walls 12 include an inflatable element 18 which is inflated or deflated to change the size of the orifice 14. The inflatable element 18 may be formed by bonding two sheets of material 22 together to form the wall 12. The sheets 22 are bonded together around the orifices 14 and a hole is cut to form the orifice 14. Inflation of the space between the sheets 22 causes the inflatable element to expand thereby reducing the size of the orifice 14. A control element 24 is releasably coupled to the membrane 4 and is configured to extend out of the patient after the membrane 4 has been implanted into the patient. The control element 24 permits the user to change the size of the orifice 14 after introducing the prosthesis 2 into the patient. The control element 24 has a lumen coupled to a source of fluid (not shown) and may be provided with a releasable connection to the membrane 4 in any suitable manner. Although the control element 24 is configured to hydraulically alter the size of the orifice 14, the control element 24 may accomplish the change in orifice 14 size using any other method such as mechanical or electrical. For example, the size of the orifice 14 could be modified using a suture which cinches the orifice 14 to reduce the size of the orifice 14.

Figure 7:
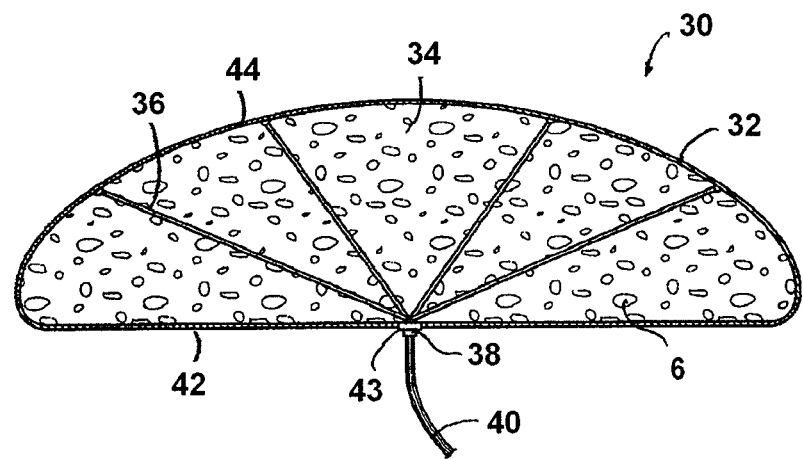
FIG. 7 shows another implantable prosthesis having tension elements which may be selectively tensioned by the user.
Figure 8:
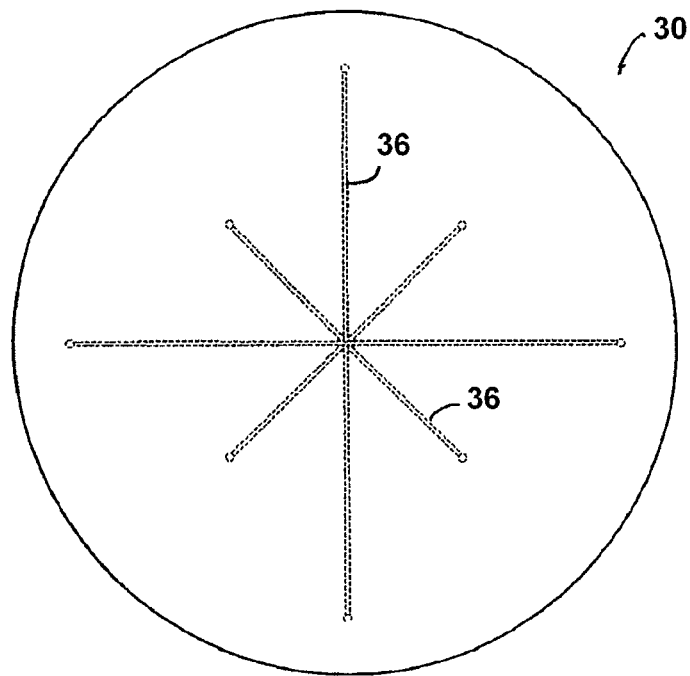
FIG. 8 shows a plan view of the prosthesis of FIG. 7.

Referring to FIGS. 7 and 8, another implantable prosthesis 30 is shown. The prosthesis 30 includes a membrane 32 which holds the flowable substance 6. The membrane 32 may be filled with an open-cell structure 34 as described above. The prosthesis 30 also includes one or more tension elements 36 which extend between two portions of the wall of the membrane 32 to help maintain a more stable shape. The tension elements 36 may extend through a valve 38 in the prosthesis 30 which permits the tension element 36 to slide therethrough while still maintaining a fluid tight seal. The tension element 36 is coupled to a control element 40 which may simply be a portion of the tension element 36 which extends out of the prosthesis 30. The tension elements 36 may extend from a posterior wall 42 to an anterior wall 44 of the membrane 32 but may, of course, be coupled to other parts of the membrane 32 as well.

The control element 40 is configured to extend out of the patient when the prosthesis 30 is implanted so that the user may adjust tension on the tension element 36 after implantation. Tension may be applied to one or more of the tension elements 36 to create a desirable texture and feel to the prosthesis 30. After the desired tension has been applied, the control element 40 may be removed by simply cutting the control element 40 or releasing the control element 40 using any other suitable method. A locking element 43 is coupled to the membrane 32 which automatically secures the tension element 36 after tension has been increased with the control element 40. The control element 40 may, of course, be manipulated prior to implantation of the prosthesis 30.

Figure 9:
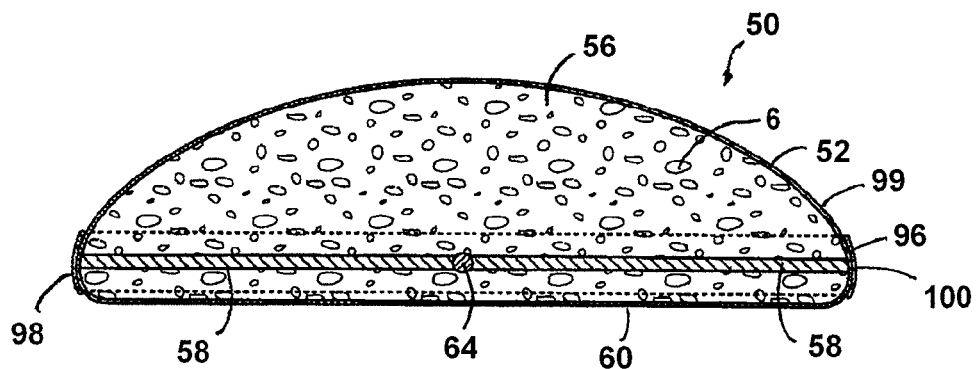
FIG. 9 shows another implantable prosthesis having tension members.
Figure 10:
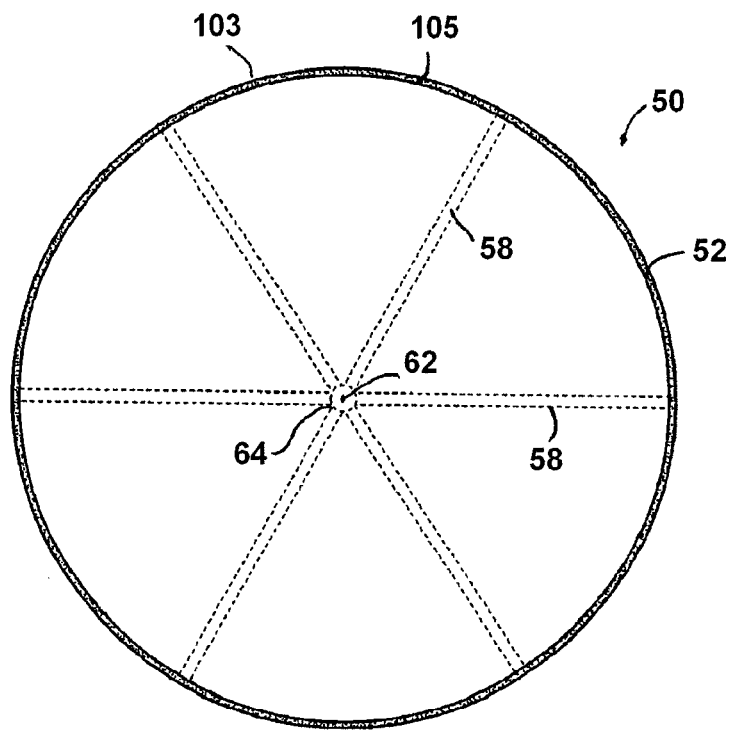
FIG. 10 shows a plan view of the prosthesis of FIG. 9.

Referring to FIGS. 9 and 10, still another implantable prosthesis 50 is shown. The prosthesis 50 includes a membrane 52 which holds the flowable substance 6. The membrane 52 may also contain an open-cell structure 56 which dampens fluid motion although the invention may be practiced without the open-cell structure 56. A plurality of tension members 58 extend through the open-cell structure 56 and are attached to the membrane 52 at both ends. The membrane 52 may have a round posterior wall 60 which is symmetrical about an axis of symmetry 62. The tension members 58 may extend from one side of the membrane 52 to a diametrically opposed side of the membrane 52. The tension members 58 may also be symmetrically arranged relative to the axis of symmetry 62 and may be coupled together at a junction 64 so that tension is distributed among the tension members 58.

Figure 11:
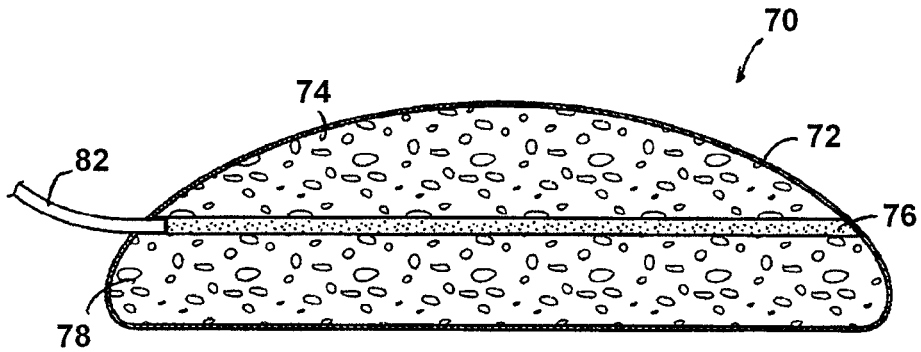
FIG. 11 shows another implantable prosthesis having a chamber which may be filled or evacuated.
Figure 12:
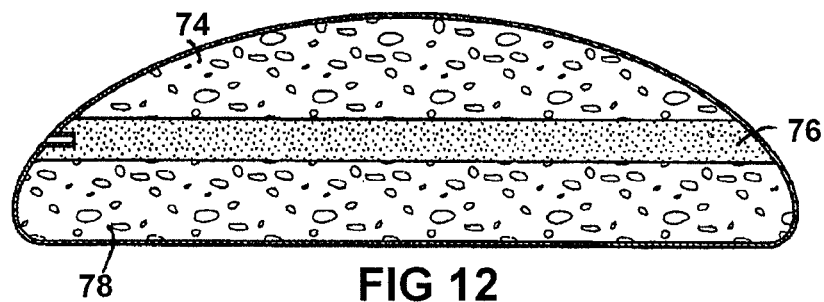
FIG. 12 shows the chamber of FIG. 11 expanded.
Figure 13:
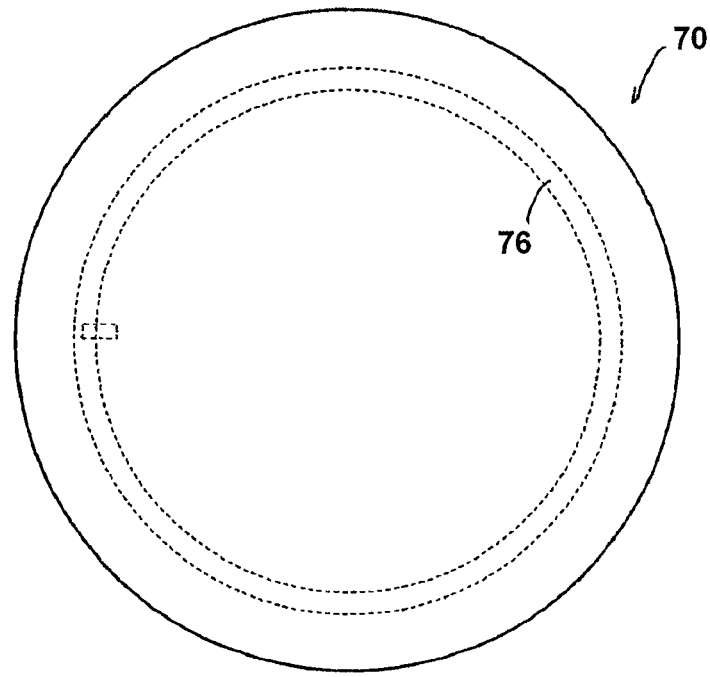
FIG. 13 is a plan view of the implantable prosthesis of FIG. 12.

Referring to FIGS. 11-13, yet another implantable prosthesis 70 is shown. The prosthesis 70 includes a membrane 72 having a first chamber 74, a second chamber 76 and a third chamber 78. The chambers 74, 76, 78 may be filled with an open-cell structure 80. The second chamber 76 is fluidly isolated from the first and third chambers 74, 78 and may be filled using a removable fill line 82. The second chamber 76 may be filled or evacuated as desired before or after the prosthesis 70 has been implanted into a patient. The second chamber 76 is positioned between the first and third chambers

74, 78 and may generally lie in a plane but may be oriented in any other suitable manner. The first and third chambers 74, 78 may be fluidly isolated from one another or may be fluidly coupled together.

Figure 14:
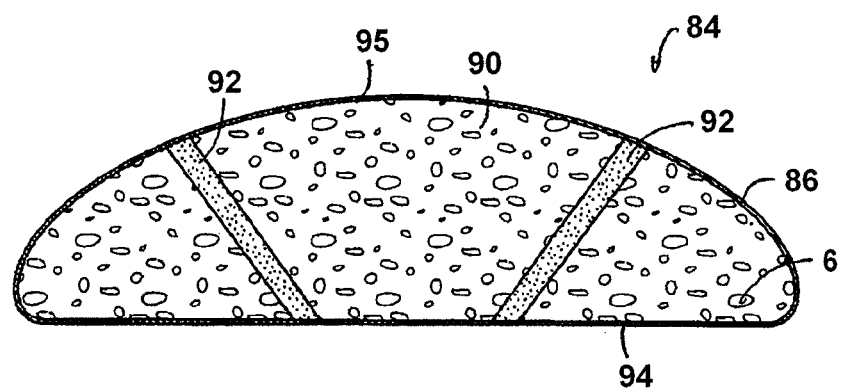
FIG. 14 shows another implantable prosthesis.
Figure 15:
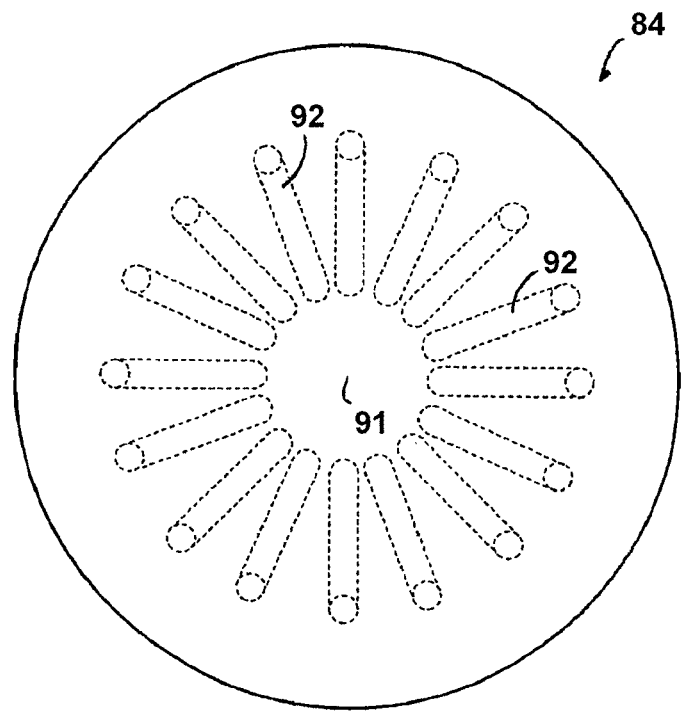
FIG. 15 is a plan view of the implantable prosthesis of FIG. 14.

Referring to FIGS. 14 and 15, another implantable prosthesis 84 is shown. The prosthesis includes a membrane 86 filled with the flowable substance 6. The prosthesis 84 also includes an open-cell structure 90 which dampens fluid motion and helps to maintain a desired shape. The open-cell structure 90 includes a plurality of voids 92 which are substantially larger than an average cell size in the open-cell structure 90. The membrane 86 may be symmetrical about an axis of symmetry 91 which is centrally located relative to a round posterior wall 94. The round posterior wall 94 and symmetrical shape permit the user to implant the device without requiring a particular orientation when implanted. The voids 92 are preferably symmetrically positioned relative to the axis of symmetry 91. The voids 92 may be elongate channels 96 cut into the open-cell structure 90 which extend from the posterior wall 94 to an anterior wall 95 of the prosthesis 84.

Referring again to FIGS. 1 and 9, a cover 96 may be used to cover a portion of an outer surface 99 of the membrane 4 and may be used with any of the implants described herein. The cover 96 may be a strip 98 of expanded PTFE which extends over, and essentially parallel to, an area commonly referred to as the waist 100. The waist 100 is generally defined as a radially outer portion of the membrane 52 when the membrane 52 is supported by the posterior wall 60 as shown in FIG. 9. The cover 96 is positioned so that at least 80% of the ePTFE is positioned no more than 1 cm from the waist 100. Positioning the ePTFE cover 96 in this manner provides the advantages of ePTFE, such as the promotion of in-growth, without the high cost of covering the entire implant with ePTFE as has been suggested by some prior art devices. Of course, numerous aspects of the present invention may be practiced without the cover 96 or with the cover 96 extending around the entire outer surface or a substantial portion thereof without departing from those aspects of the invention.

The cover 96 may be applied to the membrane 52 in the following manner when using the strip 98 of ePTFE. The membrane 52 is held at two spaced-apart locations 103, 105 along the waist 100 and the membrane 52 is stretched to increase the space between these locations. The membrane 52 may be held by a curved work element which supports the curved shape of the membrane when the membrane 52 is stretched. The strip 98 is then attached to the membrane at both locations 103, 105 and the membrane 52 is then released to release tension on the membrane 52. This process may be repeated until the entire waist 100 is covered by the strip 98. In one embodiment, the strip 98 is attached at 6-10 locations around the periphery of the waist 100.

Figure 17:
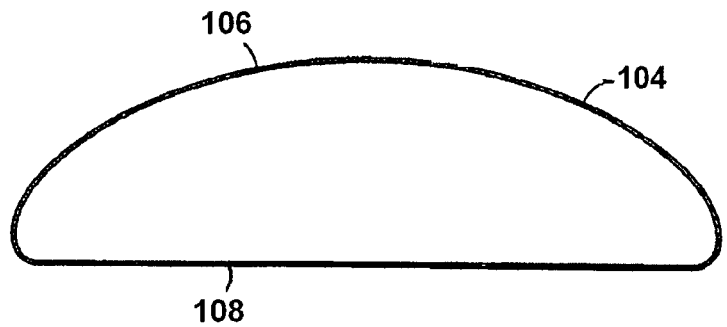
FIG. 17 shows a membrane which is smaller than the open cell structure of FIG. 16.

Referring now to FIGS. 16 and 17, still another aspect of the present invention is shown. An open cell structure 102 is provided which has a natural, unbiased shape which is larger than membrane 104. The open cell structure 102 is compressed within the membrane 104 which holds the open cell structure 102 in a compressed state. The open cell structure 102 may occupy a volume when in the natural unbiased shape which is 5% to 20% larger than the volume of the membrane 104.

The open cell structure 102 may be larger than the membrane 104 in all dimensions or may be selectively larger in one or more dimensions. For example, the open cell structure 100 may have a height H which is 5% to 20% larger than a maximum dimension between an anterior wall 106 and a posterior wall 108. The open cell structure 102 may also have a width W which is 5% to 20% larger than a maximum outer dimension or diameter of the posterior wall 108.

Figure 18:
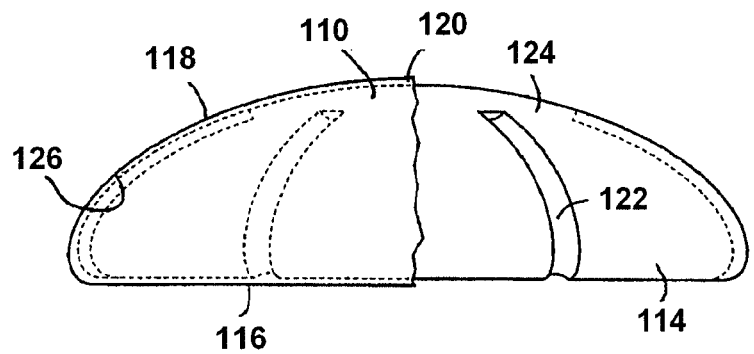
FIG. 18 shows another implantable prosthesis.
Figure 19:
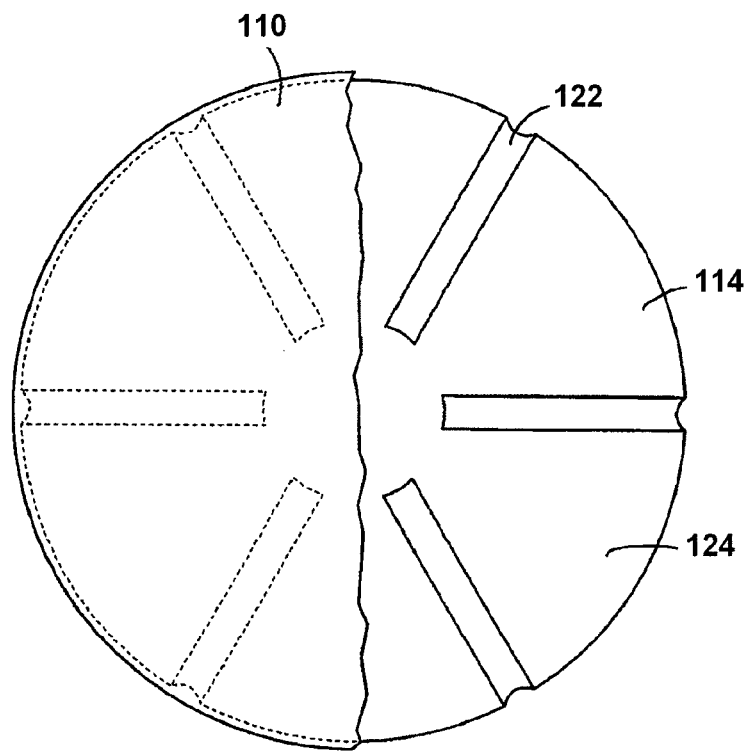
FIG. 19 is a plan view of the implantable prosthesis of FIG. 18.
Figure 20:
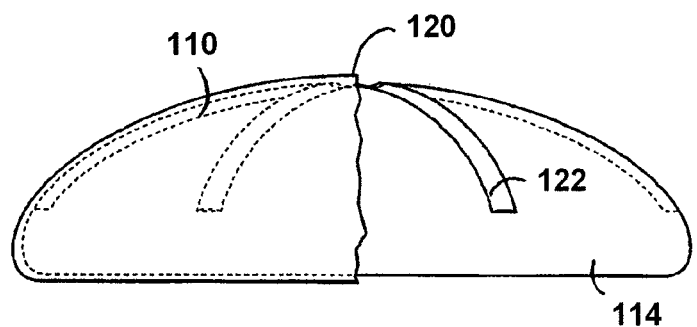
FIG. 20 shows still another implantable prosthesis having radially oriented channels.
Figure 21:
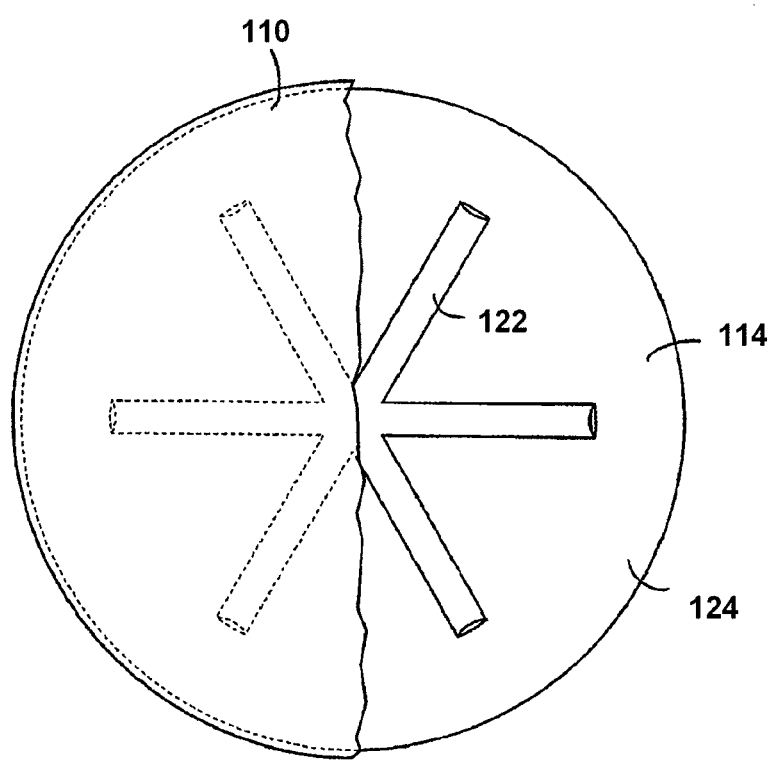
FIG. 21 is a plan view of the implantable prosthesis of FIG. 20.
Figure 22:
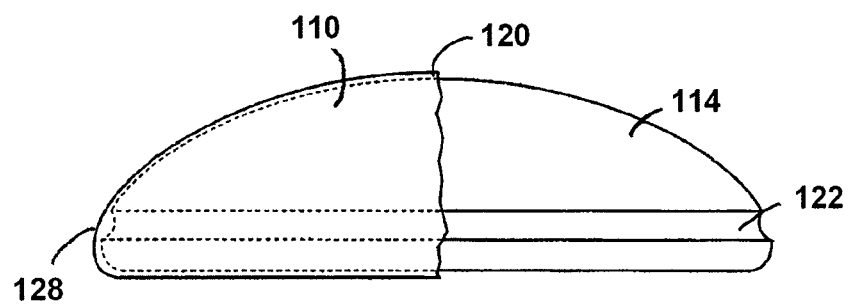
FIG. 22 shows another implantable prosthesis having circumferential channels.
Figure 23:
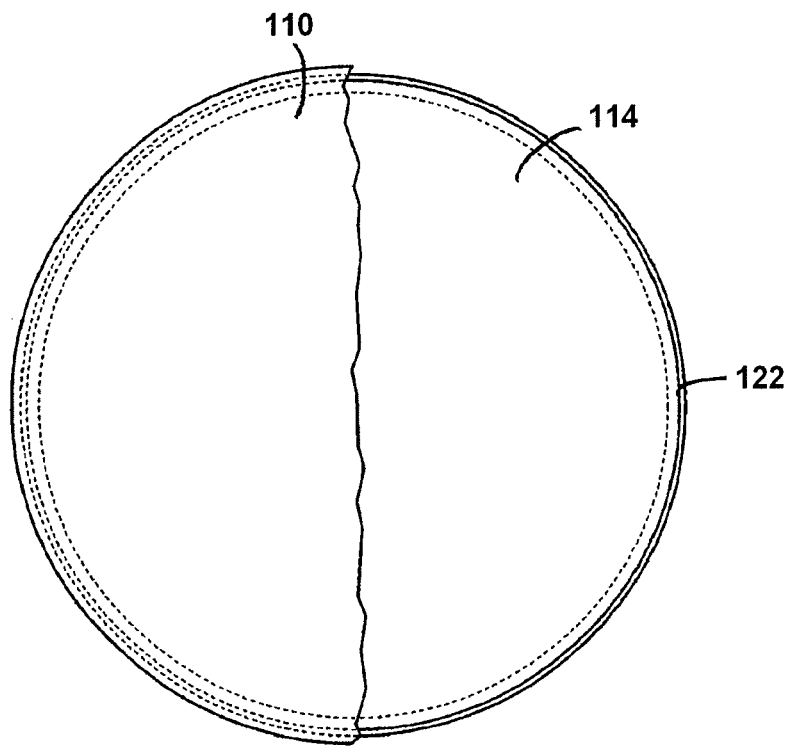
FIG. 23 is a plan view of the implantable prosthesis of FIG. 22.
Figure 24:
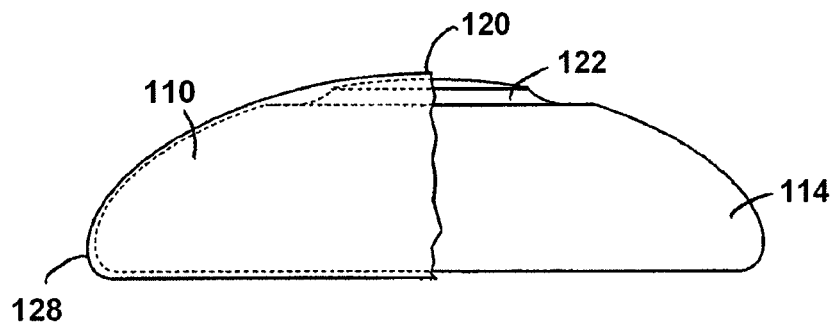
FIG. 24 shows still another implantable prosthesis with a circumferential channel.
Figure 25:
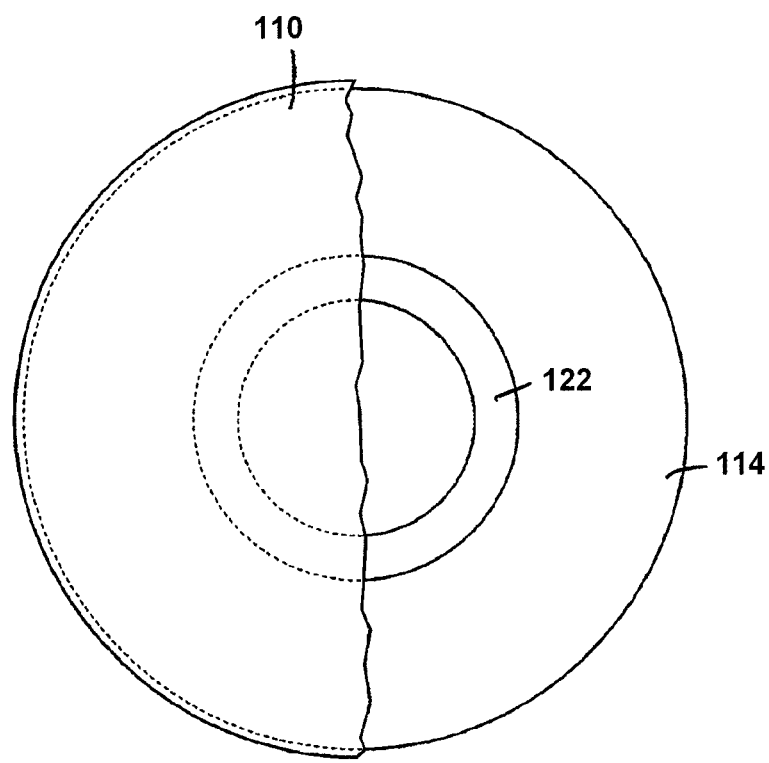
FIG. 25 is a plan view of the implantable prosthesis of FIG. 24.

Referring now to FIGS. 18-25, an implantable prosthesis 109 is shown which has a membrane 110 and an open cell structure 114 with channels 122 formed in an outer surface 124 of the open cell structure 114. The membrane 110 includes a posterior wall 116 and an anterior wall 118 having an apex 120. The channels 122 may be positioned adjacent to an inner surface 126 of the membrane 110 so that the flowable substance can flow in a more unrestricted manner in the channels 122 than in the open cell structure 114. The channels 122 may extend radially relative to the apex 120 of the membrane 112 (FIGS. 18-21). The channels 120 may intersect one another at the inner surface 126 of the membrane 112 below the apex 120 (FIGS. 20 and 21) or may be non-intersecting (FIGS. 18 and 19). Referring to FIGS. 22 and 23, the channel 122 may also extend circumferentially about the outer surface 124 of the open cell structure 114. The channel 122 may also be positioned adjacent to a waist 128 of the membrane which is a radially outer portion of the membrane 110 near the posterior wall 116 as described above. The channel 122 may also extend around the apex 120 of the membrane 110 at a position nearer to the apex 120 than to the waist 128 as shown in FIGS. 24 and 25.

Figure 26:
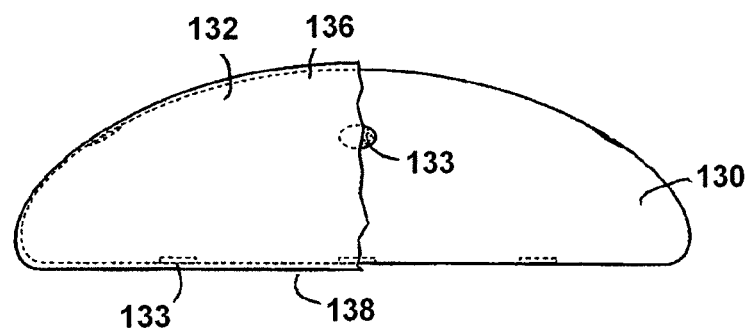
FIG. 26 shows another implantable prosthesis with a selective number of discrete attachments along the posterior and anterior walls.
Figure 27:
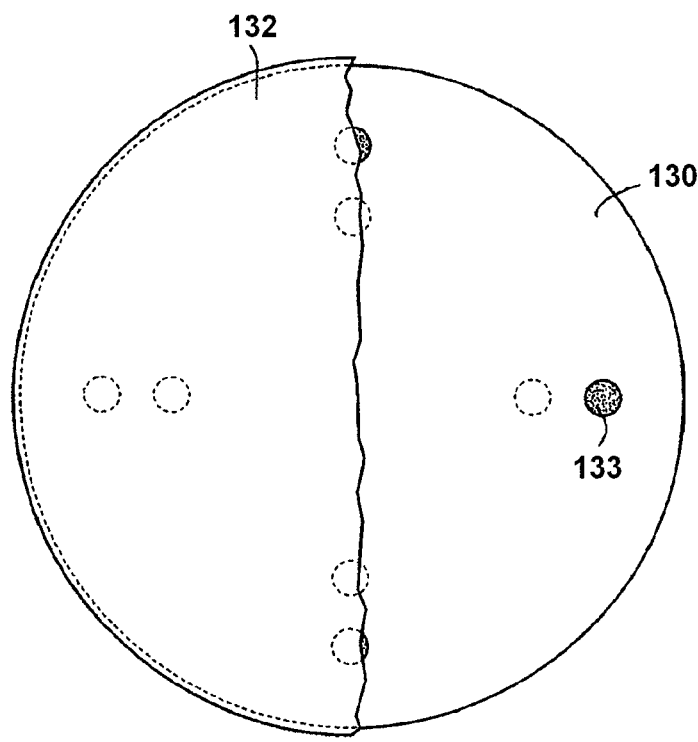
FIG. 27 is a plan view of the prosthesis of FIG. 26.
Figure 28:
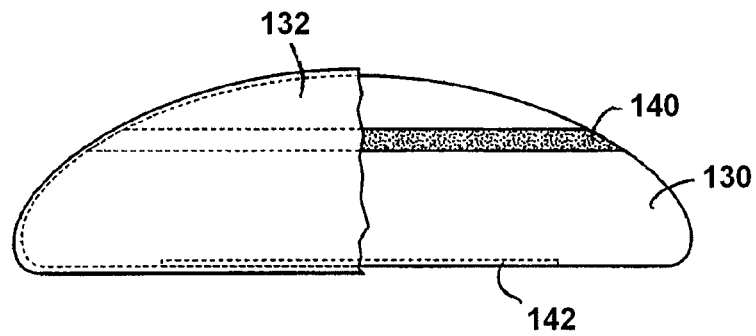
FIG. 28 shows an implantable prosthesis which is attached to the membrane along two circular strips.
Figure 29:
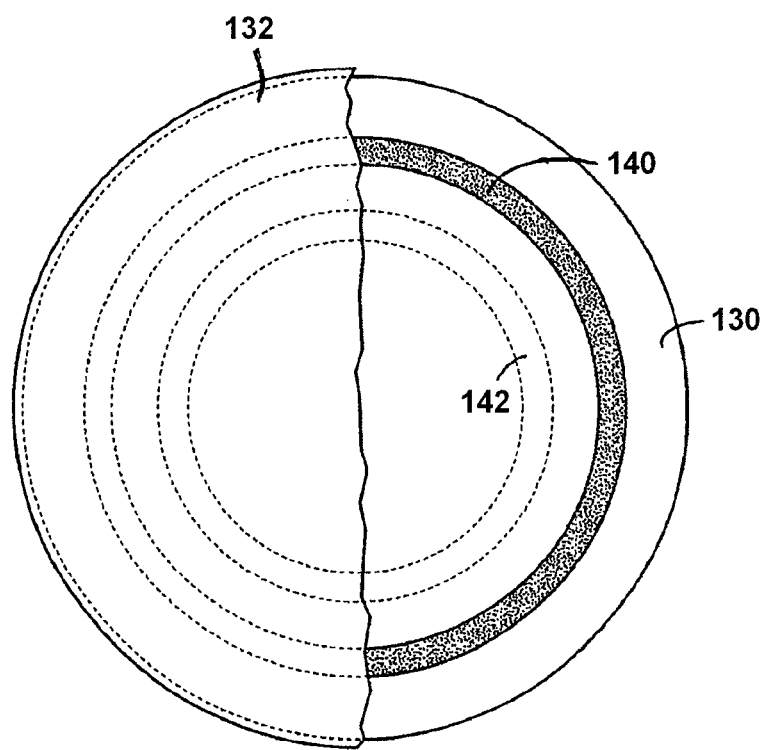
FIG. 29 is a plan view of the prosthesis of FIG. 28.

Referring now to FIGS. 26-29, open cell structure 130 may be attached to membrane 132 at a selective number of locations which are separated by portions of the open cell structure 130 which are free to move relative to an inner surface 134 of the membrane 132. FIGS. 26 and 27 shows the open cell structure 130 attached to the membrane 132 at four spaced apart locations on anterior wall 136 and posterior wall 138. FIGS. 28 and 29 show the open cell structure 130 attached to the membrane 132 along a strip 140 on the anterior wall 136 and along a strip 142 on the posterior wall 138. The strip 136 on the anterior wall 136 may form a closed loop that encircles the apex of the membrane.

Figure 30:
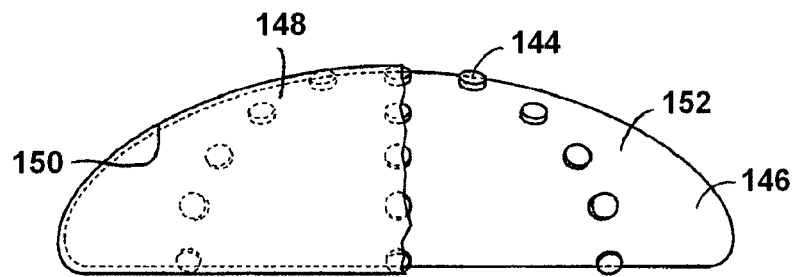
FIG. 30 shows a plurality of spacers positioned between the membrane and the open cell structure.
Figure 31:
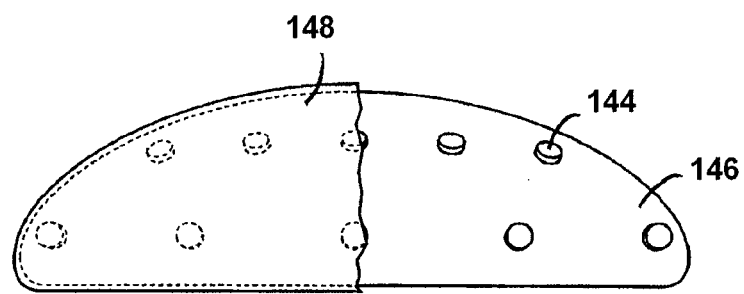
FIG. 31 shows another embodiment having a plurality of spacers.

Referring now to FIGS. 30 and 31, spacers 144 may also be provided between open cell structure 146 and the membrane 148. The spacers 144 create an area between the membrane 148 and the open cell structure 146 so that the flowable substance may flow in a less restricted manner in this area as compared to within the open cell structure 146. The spacers 144 may be attached to the membrane 148 or to the open cell structure 146 and may be integrally formed with either part. When attached to the open cell structure 146, the spacers 144 are free to slide against an inner surface 150 of the membrane 148. The spacers 144 may be sized and positioned so that less than 20% of an outer surface 152 of the open cell structure 146 is covered by the spacers 144. Stated another way, at least 80% of the outer surface 152 of the open cell structure 146 is free to move relative to the inner surface 150 of the membrane 148. The spacers 144 may be arranged in a radially oriented fashion (FIG. 30) or in a circumferential pattern (FIG. 31) or any other suitable configuration without departing from the scope of the invention.

The present invention has been described in connection with various preferred embodiments and it is understood that modifications and alterations of these embodiments may be accomplished while remaining within the scope of the invention as defined by the claims. For example, the implants may be anatomical implants rather than symmetrical implants without departing from the scope of various aspects of the invention. Furthermore, the various aspects of the invention have been described independently but may, of course, be practiced together and such combinations are expressly incorporated. For example, the spacers 144 of FIGS. 30 and 31 could be used in combination with the tension elements 36 of FIGS. 7 and 8.

What is claimed is:

1. An implantable breast prosthesis, comprising:
    a soft, flexible outer membrane comprising a convex anterior wall and a flat posterior wall, the membrane having a volume, a maximum height, and a maximum diameter of the posterior wall;
    a flowable substance contained within the membrane and configured to flow within the membrane, wherein the flowable substance comprises saline or water; and
    an open cell structure positioned inside the membrane, the open cell structure being filled with the flowable substance so that the open cell structure dampens motion of the flowable substance within the membrane,
    wherein the open cell structure has a natural, unbiased shape when not positioned inside the membrane, the natural, unbiased shape being larger than the membrane,
    the membrane holding the open cell structure in a compressed state when the open cell structure is positioned inside the membrane, the compressed state being smaller than the natural, unbiased shape, and
    wherein the open cell structure has a volume in its natural, unbiased shape that is 5% to 20% larger than the volume of the membrane, and
    wherein the natural, unbiased shape of the open cell structure has at least one of (1) a height which is 5% to 20% larger than the maximum height of the membrane and (2) a diameter which is 5% to 20% larder than the maximum diameter of the posterior wall.

2. The implantable breast prosthesis, of claim 1, further comprising: a tension element coupled to the membrane at a first location and a second location; and a control element coupled to the tension element, the control element being configured to increase tension on the tension element so that the tension element draws the first and second locations toward one another.

3. The implantable breast prosthesis of claim 2, wherein the control element is configured to extend out of a patient when the membrane has been implanted into the patient so that tension on the tension element may be altered after the membrane has been implanted into the patient.

4. The implantable breast prosthesis of claim 2, wherein the first location being on the posterior wall and the second location being on the anterior wall.

5. The implantable breast prosthesis of claim 2, further comprising a plurality of tension elements extending within the membrane, each of the tension elements being configured to be tensioned independently by a user after introduction of the membrane into the patient.

6. The implantable breast prosthesis of claim 1, further comprising a plurality of elastic tension elements extending through the open-cell structure coupled to the membrane, each tension element having a first end and a second end which are both attached to the membrane.

7. The implantable breast prosthesis of claim 1, further comprising a plurality of voids in the open-cell structure which are substantially larger than the cells of the open-cell structure.

8. The implantable breast prosthesis of claim 7, wherein the plurality of voids are organized in a symmetrical pattern relative to an axis of symmetry.

9. The implantable breast prosthesis of claim 7, wherein plurality of voids are elongate channels which extend through the open-cell structure.

10. The implantable breast prosthesis of claim 1, further comprising a cover material;
    the membrane having an outer surface and a waist, the waist being an outer ring which is positioned between the anterior wall and the posterior wall when the membrane is supported by the posterior wall;
    the cover material extending over the membrane and being made of expanded PTFE, wherein at least 80 percent of the expanded PTFE which covers the membrane is positioned no more than one centimeter from the waist of the membrane.

11. The implantable breast prosthesis of claim 10, wherein the outer surface of the membrane is exposed to tissue when implanted into a patient except for the portion of the outer surface covered by the cover material.

12. The implantable breast prosthesis of claim 10, wherein the cover material is a strip which wraps around the membrane in a direction which is parallel to the waist so that the strip covers the outer surface of the membrane along the waist.

13. The implantable breast prosthesis of claim 1, wherein the membrane includes an inner surface which is exposed to the flowable substance; and the open cell structure includes a channel extending along an outer surface of the open cell structure adjacent to the inner surface of the membrane.

14. The implantable breast prosthesis of claim 13, wherein the anterior wall has an apex; and the open cell structure includes a plurality of channels which intersect along the inner surface of the membrane below the apex.

15. An implantable prosthesis, comprising:
    a soft, flexible outer membrane, the membrane having a volume, a maximum height, an outer surface, a posterior wall, an anterior wall, and a waist, the waist being an outer ring portion of the membrane which is positioned between the anterior wall and the posterior wall when the membrane is supported by the posterior wall, the membrane having a maximum diameter at the waist when the membrane is supported by the posterior wall;
    a flowable substance contained within the membrane and configured to flow within the membrane, wherein the flowable substance comprises saline or water;
    an open cell structure positioned inside the membrane, the open cell structure being filled with the flowable substance so that the open cell structure dampens motion of the flowable substance within the membrane; and
    a cover material, the cover material extending over the waist of the membrane and being made of expanded PTFE, wherein at least 80 percent of the expanded PTFE is positioned no more than one centimeter from the waist of the membrane;
    wherein the open cell structure has a natural, unbiased shape when not positioned inside the membrane, the natural, unbiased shape being larger than the membrane,
    the membrane holding the open cell structure in a compressed state when the open cell structure is positioned inside the membrane, the compressed state being smaller than the natural, unbiased shape, and
    wherein the open cell structure has a volume in its natural, unbiased shape that is 5% to 20% larger than the volume of the membrane, and
    wherein the natural, unbiased shape of the open cell structure has at least one of (1) a height which is 5% to 20% larger than the maximum height of the membrane and (2) a diameter which is 5% to 20% larder than a maximum outer diameter of the posterior wall.

* * * * *